Figure 1:
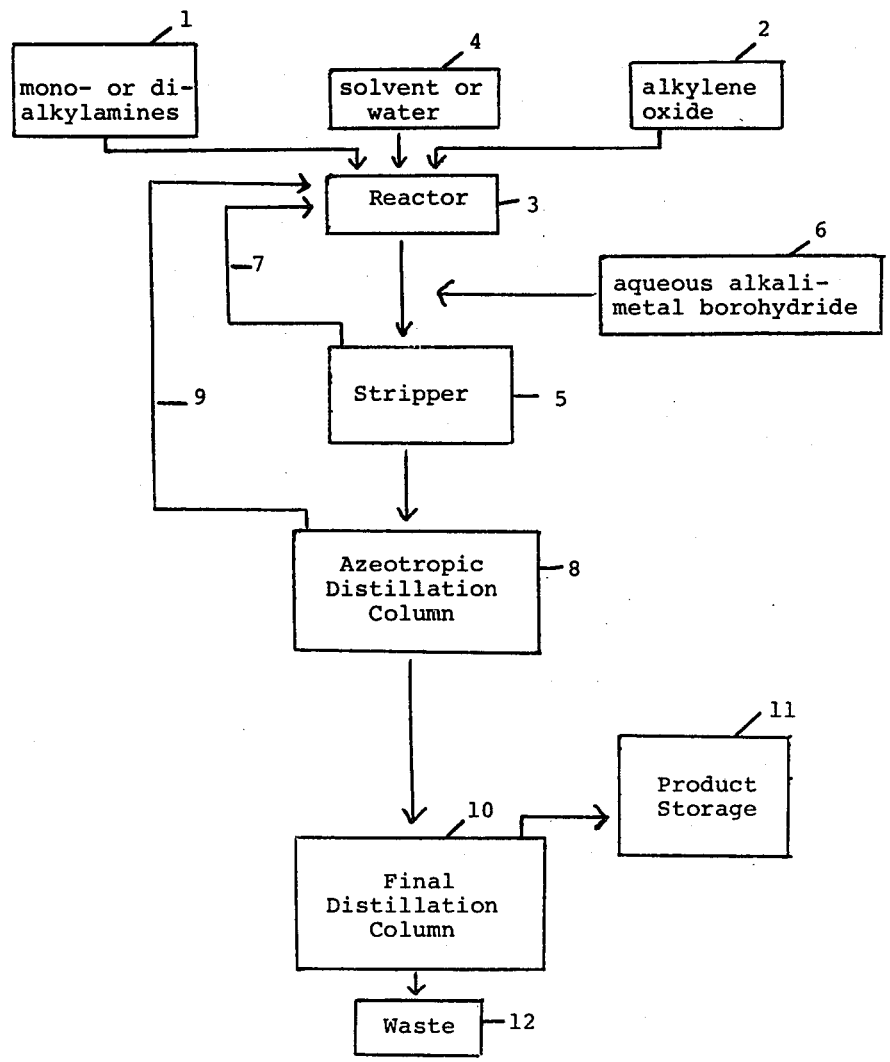

United States Patent [19]

Gardner

[11] 4,379,024

[45] Apr. 5, 1983

[54] PROCESS FOR THE MANUFACTURE OF ALKYLAMINOALKANOL

[75] Inventor: David M. Gardner, Worcester, Pa.

[73] Assignee: Pennwalt Corporation, Philadelphia, Pa.

[21] Appl. No.: 286,211

[22] Filed: Jul. 23, 1981

[51] Int. Cl.³ .............................................. B01D 3/34
[52] U.S. Cl. ......................................... 203/6; 203/31; 203/32; 564/503
[58] Field of Search ....................... 203/28, 29, 31, 32, 203/36, 37, 6; 564/503

[56] References Cited

U.S. PATENT DOCUMENTS 2,867,651  1/1959  Wise ....................................... 203/32
3,207,790  9/1965  Glew et al. .
3,428,469  2/1969  Cyba et al. ........................... 564/503
3,860,520  1/1975  Lindemuth et al. ................... 203/39

Primary Examiner—Frank Sever

[57] ABSTRACT

Color-stable alkylaminoalkanol is prepared by adding, prior to stripping-off excess reactant, an alkali metal borohydride to the reaction product of alkylene oxide and an excess of primary or secondary amine and thereafter distilling the reaction mass to recover residual and reacted (borates) alkali metal borohydride and reduced color-forming bodies as bottoms and alkylaminoalkanol as distillate. If water is present in the reaction between the alkylene oxide and primary or secondary amine, the reaction mass is distilled after recovery of excess amine to recover an azeotrope of the product which is recycled to the reactor.

6 Claims, 1 Drawing Figure

PROCESS FOR THE MANUFACTURE OF ALKYLAMINOALKANOL

This invention relates to a novel process for preparing color-stable N-alkylaminoalkanol referred to hereinafter as alkylaminoalkanol. Alkylaminoalkanols are used as starting materials in the preparation of surface-active agents, as catalysts in the manufacture of urethanes from organic isocyanates and hydroxy-containing compounds, as intermediates in preparing textile agents and substances having bactericidal and fungicidal properties, and as components of insecticidal and textile-conditioning formulation. In virtually all of these applications it is preferred that the alkylaminoalkanols be pure, colorless materials.

BACKGROUND

In the usual preparative method for alkylaminoalkanols, an alkylamine is reacted with alkylene oxide at an elevated temperature and pressure in either the absence or presence of solvents. The unconverted reactants, and solvents, if used, are stripped from the crude product and, where possible, recycled; the crude product is then distilled to obtain the pure material. Alkylaminoalkanol, in general, and dialkylaminoethanol, in particular, when freshly prepared, is a water-white or nearly water-white liquid. However, after standing, it will darken in color. This darkening occurs regardless of whether or not the alkylaminoalkanol is exposed to light and regardless of whether or not it is sealed from atmospheric air. This darkening is objectionable for many end-uses. Inhibition of color formation has been accomplished in the past by addition to the product of mono- or di- lower alkanolamine (U.S. Pat. No. 3,567,779), and by addition of an alkali or alkaline earth metal borate (U.S. Pat. No. 3,742,059). Other patents dealing with inhibition of discoloration of alkylaminoalkanol included U.S. Pat. No. 2,422,503 and 3,159,276. In U.S. Pat. No. 3,131,132 a process is described for treating the reaction product of ethylene oxide and dimethylamine with an acid prior to distillation of the final product to thereby provide a dimethylaminoethanol that remains colorless on storage. In U.S. Pat. No. 3,207,790 a process of removing color from alkylaminoalkanol by addition of a borohydride of alkali metal (which may be followed by distillation) is described. None of these disclosures suggests the process of the present invention.

THE INVENTION

The present invention provides a process for preparing a color-stable alkylaminoalkanol by the reaction of alkylene oxide with an excess of the class of a primary or secondary amine, which comprises the steps of (1) adding to the product of the reaction prior to removal of excess amine at least about one mole of alkali metal borohydride per 1650 mole of alkylene oxide used in the reaction, (2) stripping-off excess amine reactant by distillation, and (3) distilling the resultant reaction mass to recover the residual and reacted alkali metal borohydride and reduced color-forming bodies as bottoms and alkylaminoalkanol as distillates.

The present invention is particularly valuable in processes in which the reaction of amine with alkylene oxide occurs in the presence of water because the technique of adding the alkali metal borohydride permits the azeotrope necessarily formed with alkylaminoalkanol when one dries the product by distillation to be recycled into the reaction mass thereby avoiding loss of the product contained in the azeotrope and eliminates the need either to recover the product from the azeotrope or to dispose of the azeotrope; it has been observed that under the reaction conditions of the present invention the alkylene oxide acts preferentially with the amine reactant rather than with the hydroxyl of the alkylaminoalkanol. When an attempt is made to recycle this azeotrope without prior addition of alkali metal borohydride, color bodies form to an intolerable degree. It has, therefore, been the practice in the industry prior to the present invention to discard the alkylaminoalkanol azeotrope.

FIG. 1 shows a flow sheet of the instant invention.

The invention will be more readily understood by reference to the flow sheet. In the flow sheet reactants mono- or dialkylamines (1) and alkylene oxide (2) are added to Reactor (3). In the preferred embodiment water (4) is also added to the Reactor. The reaction mass passes from the Reactor to Stripper (5) along with aqueous alkali metal borohydride (6) Excess amine reactant is returned via line (7) from the Stripper to the Reactor. After removal of unreacted components, the reaction mass moves to the Azeotropic Distillation Column (8) where the reaction mass is dried by removal of the alkylaminoalkanol azeotrope which is returned to the reactants via line (9). The dried reaction mass is thereafter finally distilled in Final Distillation Column (10) from which the color-stable product is removed as the overhead and collected in Product Storage (11) while the residual and reacted added metal borohydride and reduced color forming bodies are removed as the bottoms and discarded as Waste (12).

EXAMPLE

This example is intended to illustrate the invention; it is not intended to limited it in any fashion. Reactant streams of 28.4 mole percentage ethylene oxide, 62.6 mole percentage diethylamine and 9 mole percentage water are fed into a reactor maintained at about 150° C. at autogeneous pressure. The crude aqueous product is withdrawn continuously and mixed with aqueous sodium borohydride (added as a 12% solution in 50% caustic) in a proportion of at least 1 mole sodium borohydride per 1603 moles ethylene oxide used in the reaction. The resultant mixture is fed to a stripper column where unreacted diethylamine is distilled overhead and recycled to the reactor. The bottoms to the stripper column are fed to an azeotrope column where the crude product is dried by distilling overhead an azeotrope containing 25.6% diethylaminoethanol boiling at 99.4° C. (1 atmosphere). The azeotrope is recycled to the reactor. The crude dried product is finally purified by distillation at reduced pressure. The diethylaminoethanol produced in this manner remains water-white after months of storage at ambient conditions. The distillation bottoms, containing the residual and reacted borohydride and reacted color-bodies, are discarded as waste.

DISCUSSION OF THE INVENTION

The reaction at elevated temperature of alkylene oxide such as ethylene oxide or propylene oxide with mono- or dialkylamines to produce mono- or dialkylaminoalkanols is well known. Generally, the reaction is conducted in a closed container at autogenous pressure. The reaction can occur in the presence of an organic solvent (such as methanol or water). Combination of the reactants in the absence of any solvent is known but requires careful control to avoid uncontrolled reactions and undesirable by-products. While the present invention, i.e. the use of the alkali metal borohydride addition prior to the removal of unreacted amine, can be used in any of these techniques, the invention is of particular advantage in those reactions that occur in the presence of water. Previously the azeotrope which forms with the alkylamine when one attempts to dry the product had to be discarded because of rapid buildup of "color-bodies" which resulted ultimately in production of a colored product. Thus, the present invention, as it relates to the use of the water-solvent system, provides an obviously improved yield (resulting from the ability to recycle the azeotrope) and the elimination of a relatively large liquid waste disposal problem which the azeotrope previously presented. The composition of typical azeotropes under different conditions is shown in the table below:

TABLE

| dialkylaminoethanol | T(°C.) | P(mm Hg) | Azeotrope Composition % Dialkyl-aminoethanol |
|---|---|---|---|
| dimethylaminoethanol | 102° | 760 | 14.5% (by wt) |
| dimethylaminoethanol | 56° | 125 | 0.9% |
| diethylaminoethanol | 99.4° | 760 | 25.6% |
| diethylaminoethanol | 55.0° | 109 | 10.0% |

Obviously, the improvement of providing a clear color-stable product applies to all three preparative techniques.

In combining the reactants, it is important to use an excess of the alkylamine so that the alkylene oxide is completely consumed in the reaction. Generally, a mole ratio of alkylamine to alkylene oxide of 1.5–2.5 is used. When water is a component, use of from about 5–15 mole percentage is recommended. While temperature of the reactant can be varied, it is convenient to use a temperature of above 100° C. in a closed container.

The alkali metal borohydride is added to the reaction mass prior to the stripping-off of the excess reactant. It is conveniently dissolved in a 50% aqueous caustic solution containing 10–15% of the alkali metal borohydride. (A commercial solution sold by the Ventron Corp.) It has been found that one mole of sodium borohydride per 1603 moles of ethylene oxide is adequate for purposes of the invention; obviously, larger amounts may be used without deleterious effect, but since the borohydride is eventually removed, efficiency of operation requires use of as little as possible. While the invention has been illustrated in terms of sodium salt, it is obvious that other salts may be used such as potassium and lithium.

The invention, while particularly useful in preparing dimethylaminoethanol and diethylaminoethanol, has general applicability to the preparation of alkylaminoalkanols, even those of longer chain length. Nevertheless, it is preferred that the alkyl chain length not exceed 4 carbon atoms. Similarly, any lower alkylene oxides may be employed as the other reactant in the system.

While the inventor does not wish to be bound by any theory of the chemistry of his invention, it is believed that the borohydride is at least partially hydrolyzed to the borate in the reaction mass thereby reducing the color-forming bodies which are believed to be aldehydes.

Many other variations and modifications of the above invention will be apparent to those skilled in the art from a reading of the above without departing from the scope of the present invention.

What is claimed:

1. In a process for preparing a color-stable alkylaminoalkanol by the reaction of alkylene oxide with an excess of the class of ammonia and a primary or secondary amine to form a reaction mass, the improvement which comprises the steps of (1) adding to the product of the reaction prior to removal of excess amine at least about one mole of alkali metal borohydride per 1650 mole of alkylene oxide used in the reaction (2) stripping-off excess amine reactant and (3) distilling the resultant reaction mass to recover the alkali metal borohydride and color-forming bodies as bottoms and alkylaminoalkanol as distillate.

2. The process of claim 1 wherein the reaction occurs in the presence of water and the reaction mass is dried between steps (2) and (3) by removal of the alkylaminoalkanol azeotrope by distillation which azeotrope is thereafter recycled to the reaction mass.

3. The process of claim 2 wherein the amine is diethylamine and the alkylene oxide is ethylene oxide.

4. The process of claim 3 wherein the borohydride is sodium borohydride.

5. The process of claim 2 wherein the amine is dimethylamine and the alkylene oxide is ethylene oxide.

6. The process of claim 5 wherein the borohydride is sodium borohydride.

* * * * *